(12) United States Patent
Yamashita et al.

(10) Patent No.: US 9,550,720 B2
(45) Date of Patent: Jan. 24, 2017

(54) METHOD FOR PRODUCING AN ω-HALO-2-ALKYNAL

(71) Applicant: Shin-Etsu Chemical Co., Ltd., Tokyo (JP)

(72) Inventors: Miyoshi Yamashita, Joetsu (JP); Takehiko Fukumoto, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/984,343

(22) Filed: Dec. 30, 2015

(65) Prior Publication Data

US 2016/0107969 A1    Apr. 21, 2016

Related U.S. Application Data

(62) Division of application No. 14/248,525, filed on Apr. 9, 2014, now Pat. No. 9,255,056.

(30) Foreign Application Priority Data

Apr. 12, 2013 (JP) ................................. 2013-083861

(51) Int. Cl.
| | |
|---|---|
| *C07C 45/43* | (2006.01) |
| *C07C 67/10* | (2006.01) |
| *C07C 45/42* | (2006.01) |
| *C07C 47/24* | (2006.01) |
| *C07C 67/11* | (2006.01) |
| *C07C 17/263* | (2006.01) |

(52) U.S. Cl.
CPC ........... *C07C 67/10* (2013.01); *C07C 17/2635* (2013.01); *C07C 45/42* (2013.01); *C07C 45/43* (2013.01); *C07C 47/24* (2013.01); *C07C 67/11* (2013.01)

(58) Field of Classification Search
CPC ......... C07C 67/10; C07C 67/11; C07C 69/145
See application file for complete search history.

(56) References Cited

U.S. PATENT DOCUMENTS 5,079,266 A * 1/1992 Bockowski ........... C07C 45/515
504/161

FOREIGN PATENT DOCUMENTS

| ES | 8204407 A1 | 8/1982 |
| ES | 2010719 A6 | 12/1989 |

OTHER PUBLICATIONS

Epsztein et al. Compt. rend. (1961), 252, p. 1803-1805 (disclosed in IDS).*
Camps et al. "Synthesis of the Two Isomers of the Potential Sex Pheromone of *Thaumetopoea pityocampa* (Lepidoptera, Notodontidae) and Related Model Compounds", *Chemistry Letters* pp. 703-706 (1981).
Camps et al. "Simple and Stereoselective Synthesis of Sex Pheromone of Processionary Moth *Thaumetopoea pityocampa* (Denis and Schiff.)", *J. Chem. Ecology* 9(7):869-875 (1983).
Cardillo et al. "A Stereoselective Synthesis of (Z)-13-Hexadecen-11-YNYL Acetate The Sex Pheromone of *Thaumetopoea pityocampa (Lepidoptera, Notodontidae)* (*)", *Gazzetta Chimica Italiana* 112:231-233 (1982).
Gardette et al. "Synthesis of (Z)-13-Hexadecen-11-YN-1-YL Acetate Major Component of Sex Pheromone of the Processionary Moth", *J. Chem. Ecology* 9(2):219-223 (1983).
Guerrero et al. "Identification of a Potential Sex Pheromone of the Processionary Moth, *Thaumetopoea pityocampa* (Lepidoptera, Notodontidae)", *Tetrahedron Letters* 22(21):2013-2016.
Michelot et al. "Une synthése courte et stéréosélective de L'Acécoxy-1 hexadécène-13 (Z)-yne-11: Principal constituent de la sécrétion phéromonale produits per la female vierge de la Processionnaire du pin *Thaumetopoea pityocampa* (Denis and Schiff.) (Lepidoptera, Notodontidae)", *J. Chem. Res.* 4:1043-1051 (1982).
Stille et al. "Stereospecific Palladium-Catalyzed Coupling Reactions of Vinyl Iodides with Acetylenic Tin Reagents", *J. Am. Chem. Soc.* 109:2138-2152 (1987).

(Continued)

*Primary Examiner* — Yong Chu
(74) *Attorney, Agent, or Firm* — Myers Bigel, P.A.

(57) ABSTRACT

Provided is a method for industrially producing a conjugated Z-alken-yn-yl acetate such as Z-13-hexadecen-11-yn-yl acetate which is a sex pheromone component of a pine processionary moth, and an intermediate for the conjugated Z-alken-yn-yl acetate under mild conditions at a high yield. More specifically, provided is a method for producing a conjugated Z-alken-yn-yl acetate (5) comprising the steps of: reacting an ω-halo-2-alkynal (1) with an alkylidene triphenylphosphorane (3) through a Wittig reaction to obtain a conjugated Z-alken-yn-yl halide (4), and acetoxylating the conjugated Z-alken-yn-yl halide (4) into a conjugated Z-alken-yn-yl acetate (5).

1 Claim, No Drawings

(56) References Cited

OTHER PUBLICATIONS

Bailey et al. "590. Higher Aliphatic Compounds. Part XI.* A Synthesis of DL-Ricinoleic Acid.", *J. Chem. Soc.* 3027-3032 (1957).
Epsztein et al. "Sur les aldéhydes alpha-acétyléniques contenant une autre fonctin a ubout de la chaîne", *Comptes Rendus Hebdomadaires des Seances de L'Academie Dessciences* 252:1803-1805 (1961).
Gómez-Bengoa et al. "Asymmetric synthesis of propargylic alcohols via aldol reaction of aldehydes with ynals promoted by prolinol ether-transition metal-BrØnsted acid cooperative catalysis", *Chem. Sci.* 4:3198-3204 (2013).
Khanous et al. "4-Fluoro-2-Butynal: Preparation and some examples of dienophilic properties", *J. Fluorine Chem.* 49:401-408 (1990).
LaPorte et al. "5-Hydroxyindoles by Intramolecular Alkynol-Furan Diels-Alder Cycloaddition", *J. Org. Chem.* 78:167-174 (2013).
Satoh et al. "Synthesis of Anacardic Acids, 6-[8(Z),11(Z)-Pentadecadienyl]salicylic Acid and 6-[8(Z),11(Z),14-Pentadecatrienyl]salicylic Acid", *Chem. Pharm. Bull.* 49(1):18-22 (2001).
Schade et al. "Synthesis of Polyfunctional Allenes by Successive Copper-Mediated Substitutions" *Chem. Eur. J.* 17:4232-4237 (2011).
Shani et al. "Stereoselective Synthesis of (Z)-13-Hexadecen-11-YN-1-YL Acetate, The Major Component of the Sex Pheromone of the Pine Processionary Moth (*Thaumetopoea pityocampa*)", *J. Chem. Ecology* 9(7):863-867 (1983).
Extended European Search Report corresponding to European Application No. 14163480.8 dated Jul. 9, 2014.

* cited by examiner

METHOD FOR PRODUCING AN ω-HALO-2-ALKYNAL

RELATED APPLICATION

This application is a divisional of U.S. application Ser. No. 14/248,525, filed Apr. 9, 2014, which claims priority from Japanese Patent Application No. 2013-083861, filed Apr. 12, 2013, the disclosures of which are incorporated by reference herein in their entirety.

FIELD AND BACKGROUND OF THE INVENTION

The present invention relates to methods for producing a conjugated Z-alken-yn-yl acetate and an ω-halo-2-alkynal which is an intermediate thereof, particularly to a method for producing Z-13-hexadecen-11-yn-yl acetate which is a sex pheromone component of a pine processionary moth (scientific name: *Thaumetopoea pityocampa*), which is a forest pest insect in Europe.

A pine processionary moth (scientific name: *Thaumetopoea pityocampa*) is an insect widely inhabiting European countries such as France, Italy, Spain, Portugal and Greece. It has become a problem as a forest pest insect because of feeding damage to trees such as pine and cedar. In addition, poisonous hair of the larva of this moth is known to cause a serious allergic reaction in humans, livestock, pets and the like. Moreover, in recent years, the habitat of the moth has been expanding northward from the Mediterranean region due to the effect of global warming. There is therefore a demand for the development of a novel control method of the moth.

It has been reported by A. Guerrero et al. in 1981 (A. Guerrero et. al., Tetrahedron Letters, Vol. 22, 2013-2016, 1981) that the sex pheromone component of this pine methodionary moth is Z-13-hexadecen-11-yn-yl acetate having a conjugated Z-alken-yn-yl acetate structure. Development of a control method such as mating disruption or mass trapping using this sex pheromone has therefore been expected.

The methods for producing Z-13-hexadecen-11-yn-yl acetate that have already been reported include: a method reported by F. Camps et al. and making use of an elimination reaction of a secondary tosylate and use of an organolithium compound (Spanish Patent Publication No. 2010719, Spanish Patent Publication No. 8204407, and F. Camps et. al., Chem. Lett., 703, 1981), a method reported by G. Cardillo et al. and using lithium diisopropylamide and a dehydration reaction (G. Cardillo et. al., Gazzetta Chimica Italiana, 112, 231, 1982), a method reported by J. K. Stille et al. and using an acetylene zipper reaction, an organotin compound, and diimide reduction (J. K. Stille et. al., J. Am. Chem. Soc., 1987, 109, 2138), a method reported by M. Gardette et al. and using a reaction between an organocopper lithium reagent and an acetylene compound (M. Gardette et. al., J. Chem. Ecolg., 9, 219, 1983), and a method reported by D. Michelot et al. and using a hydroboration reaction and a coupling reaction in the presence of a palladium catalyst (D. Michelot et. al., J. Chem. Res., 4, 1043, 1982). Thus, in these methods, a special raw material such as an organolithium compound, an organoboron compound, an organotin compound or a diimide compound is used and a step of requiring a low-temperature reaction at −10° C. or less for the production is comprised.

On the other hand, as a method for producing Z-13-hexadecen-11-yn-yl acetate under mild conditions without using a special raw material, there has been reported a production method using a Wittig reaction between 13-tetrahydropyranoxy-2-tridecyn-1-al obtained by protecting an alcohol group at the C13-position with a tetrahydropyranyl group and propylidene triphenylphosphorane (F. Camps et. al., J. Chem. Ecolg., 9, 869, 1983).

SUMMARY OF THE INVENTION

It has been reported in the most of the methods for producing Z-13-hexadecen-11-yn-yl acetate that a special raw material such as an organolithium compound, an organoboron compound, an organotin compound, or a diimide compound is used and a step of requiring a low temperature reaction at −10° C. or less is comprised. Accordingly, the methods have many problems for an industrial mass production to be used in practice from the standpoints of safety, production equipment, production cost and the like. The production method through a Wittig reaction which can be carried out under mild conditions is effective as an industrial production method, but has some problems such as reduction of yield owing to inclusion of more steps including protection and deprotection steps of the terminal ω-alcohol group, and a low yield in the Wittig reaction.

With the foregoing in view, the invention has been made. An object of the invention is to overcome the problems of the conventional art and provide a method for industrially producing a conjugated Z-alken-yn-yl acetate such as Z-13-hexadecen-11-yn-yl acetate which is the sex pheromone component of a pine methodionary moth and an intermediate for the conjugated Z-alken-yn-yl acetate, under mild conditions at a high yield.

The present inventors have found that use of an ω-halo-2-alkynal having a halogen group as the terminal ω-functional group and represented by formula (1):

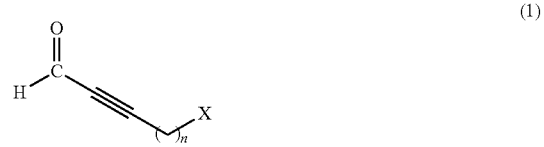

(1)

wherein X represents a halogen atom and n stands for an integer of from 2 to 15, makes it possible to produce a conjugated Z-alken-yn-yl halide without conducting protection and deprotection steps and to keep a good yield even in a subsequent Wittig reaction. They have also found that the conjugated Z-alken-yn-yl halide can be converted into a corresponding acetate at a good yield by a single step and the intended conjugated Z-alken-yn-yl acetate such as Z-13-hexadecen-11-yn-yl acetate can be produced efficiently. Such findings have led to the completion of the invention.

In the present invention, there is provided a method for producing an ω-halo-2-alkynal comprising a step of hydrolyzing an ω-halo-1,1-dialkoxy-2-alkyne represented by formula (2):

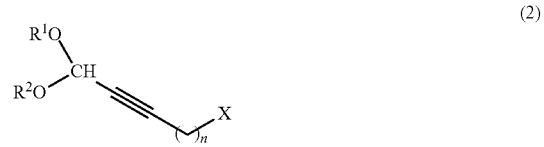

(2)

wherein R¹ and R² may be the same or different and each represents a linear,
branched or cyclic $C_{1-10}$ hydrocarbon group, X represents a halogen atom,
and n stands for an integer of from 2 to 15,
in water and an organic solvent in the presence of sulfonic acid to form a ω-halo-2-alkynal represented by the formula (1).

In the present invention, there is also provided a method for producing a conjugated Z-alken-yn-yl acetate comprising the steps of hydrolyzing an ω-halo-1,1-dialkoxy-2-alkyne represented by formula (2):

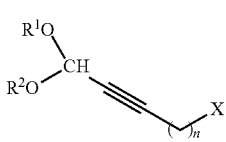

(2)

wherein R¹ and R² may be the same or different and each represents a linear,
branched or cyclic $C_{1-10}$ hydrocarbon group, X represents a halogen atom,
and n stands for an integer of from 2 to 15
in water and an organic solvent in the presence of sulfonic acid to form a ω-halo-2-alkynal represented by the formula (1), reacting the ω-halo-2-alkynal with an alkylidene triphenylphosphorane represented by formula (3):

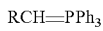 RCH=PPh₃    (3)

wherein R represents a linear, branched, or cyclic $C_{1-12}$ hydrocarbon group and Ph represents a phenyl group,
to obtain a conjugated Z-alken-yn-yl halide represented by formula (4):

(4)

and acetoxylating the conjugated Z-alken-yn-yl halide into a conjugated Z-alken-yn-yl acetate represented by formula (5):

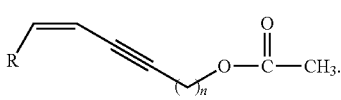

(5)

In the present invention, there is further provided an ω-halo-2-alkynal represented by formula (1) wherein n stands for an integer of from 2 to 4, 6, 7 and 10 to 15.

According to the invention, a conjugated Z-alken-yn-yl acetate such as Z-13-hexadecen-11-yn-yl acetate which is the sex pheromone component of a pine methodionary moth, can be industrially produced under mild conditions with high efficiency.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

The ω-halo-2-alkynal is represented by the following formula (1) and it is, for example, 13-chloro-2-tridecynal.

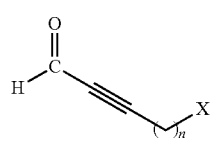

(1)

In the formula (1), X represents a halogen atom such as chlorine, bromine or iodine. Of these, chlorine and bromine atoms are particularly preferred as the halogen atom from the standpoints of a yield and availability of raw materials. In addition, n stands for an integer of from 2 to 15, preferably an integer of from 4 to 10, more preferably an integer of from 6 to 10. Specific examples of $(CH_2)_n$ include an alkylene group such as methylene, ethylene, propylene, butylene, pentylene, hexylene, heptylene, octylene, nonylene and decylene.

Specific examples of the ω-halo-2-alkynal (1) include an ω-chloro-2-alkynal such as 5-chloro-2-pentynal, 6-chloro-2-hexynal, 7-chloro-2-heptynal, 8-chloro-2-octynal, 9-chloro-2-nonynal, 10-chloro-2-decynal, 11-chloro-2-undecynal, 12-chloro-2-dodecynal and 13-chloro-2-tridecynal, and an ω-bromo-2-alkynal such as 5-bromo-2-pentynal, 6-bromo-2-hexynal, 7-bromo-2-heptynal, 8-bromo-2-octynal, 9-bromo-2-nonynal, 10-bromo-2-decynal, 11-bromo-2-undecynal, 12-bromo-2-dodecynal and 13-bromo-2-tridecynal.

The ω-halo-2-alkynal represented by the formula (1) can be produced by hydrolyzing the dialkylacetal portion of an ω-halo-1,1-dialkoxy-2-alkyne represented by the following formula (2) in water and an organic solvent in the presence of an acid catalyst. For example, 13-chloro-2-tridecynal can be produced by hydrolyzing 13-chloro-1,1-diethoxy-2-tridecyne in the presence of an acid catalyst in water and an organic solvent.

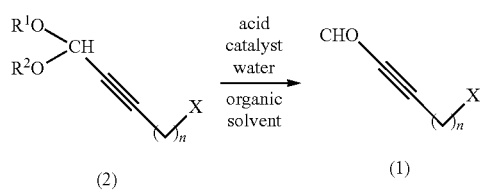

(2)  (1)

In the formula (2), $R^1$ and $R^2$ are the same or different and each represents a linear, branched or cyclic $C_{1-10}$ hydrocarbon group. Specific examples include a linear hydrocarbon group such as methyl, ethyl, propyl and butyl; a branched hydrocarbon group such as isopropyl, isobutyl, sec-butyl and tert-butyl; and a cyclic hydrocarbon group such as cyclopropyl, cyclobutyl, cyclopentyl and cyclohexyl. Preferred are a linear hydrocarbon group such as methyl, ethyl, propyl and butyl, with methyl and ethyl groups being more preferred.

X and n have the same meanings as described above and preferred examples of each of them are also as described above.

Specific examples of the ω-halo-1,1-dialkoxy-2-alkyn (2) include an ω-chloro-1,1-dimethoxy-2-alkyne such as 5-chloro-1,1-dimethoxy-2-pentyne, 6-chloro-1,1-dimethoxy-2-hexyne, 7-chloro-1,1-dimethoxy-2-heptyne, 8-chloro-1,1-dimethoxy-2-octyne, 9-chloro-1,1-dimethoxy-2-nonyne, 10-chloro-1,1-dimethoxy-2-decyne, 11-chloro-1,1-dimethoxy-2-undecyne, 12-chloro-1,1-dimethoxy-2-dodecyne and 13-chloro-1,1-dimethoxy-2-tridecyne; an ω-bromo-1,1-dimethoxy-2-alkyne such as 5-bromo-1,1-dimethoxy-2-pentyne, 6-bromo-1,1-dimethoxy-2-hexyne, 7-bromo-1,1-dimethoxy-2-heptyne, 8-bromo-1,1-dimethoxy-2-octyne, 9-bromo-1,1-dimethoxy-2-nonyne, 10-bromo-1,1-dimethoxy-2-decyne, 11-bromo-1,1-dimethoxy-2-undecyne, 12-bromo-1,1-dimethoxy-2-dodecyne and 13-bromo-1,1-dimethoxy-2-tridecyne; an ω-chloro-1,1-diethoxy-2-alkyne such as 5-chloro-1,1-diethoxy-2-pentyne, 6-chloro-1,1-diethoxy-2-hexyne, 7-chloro-1,1-diethoxy-2-heptyne, 8-chloro-1,1-diethoxy-2-octyne, 9-chloro-1,1-diethoxy-2-nonyne, 10-chloro-1,1-diethoxy-2-decyne, 11-chloro-1,1-diethoxy-2-undecyne, 12-chloro-1,1-diethoxy-2-dodecyne and 13-chloro-1,1-diethoxy-2-tridecyne; and an ω-bromo-1,1-diethoxy-2-alkyne such as 5-bromo-1,1-diethoxy-2-pentyne, 6-bromo-1,1-diethoxy-2-hexyne, 7-bromo-1,1-diethoxy-2-heptyne, 8-bromo-1,1-diethoxy-2-octyne, 9-bromo-1,1-diethoxy-2-nonyne, 10-bromo-1,1-diethoxy-2-decyne, 11-bromo-1,1-diethoxy-2-undecyne, 12-bromo-1,1-diethoxy-2-dodecyne and 13-bromo-1,1-diethoxy-2-tridecyne.

The ω-halo-1,1-dialkoxy-2-alkyne represented by the formula (2) can be produced, for example, by the method described in JP 2-101028A or JP 2005-272409A. More specifically, as described in JP 2-101028A, an ω-halo-1,1-dialkoxy-2-alkyne can be obtained by reacting an ω-halo-1-alkyne with an alkyl magnesium halide and then with an alkyl orthoformate. When the raw material used is an ω-halo-1-alkyne having a long methylene chain which is not easily available, as described in JP 2005-272409A, an ω-halo-1,1-dialkoxy-2-alkyne having a long methylene chain can be obtained by reacting the ω-halo-1-alkyne with an alkyl magnesium halide to protect the terminal alkyne, reacting the resulting product with metal magnesium to form a corresponding Grignard reagent, subjecting the Grignard reagent to a cross-coupling reaction with a 1-bromo-ω-chloroalkane in the presence of a copper halide catalyst, and then reacting the resulting product with an alkyl orthoformate. Alternatively, the ω-halo-1,1-dialkoxy-2-alkyne having a long methylene chain may be produced by isolating and purifying the ω-halo-1-alkyne having a long methylene chain after the above-mentioned cross-coupling reaction, reacting the isolated and purified ω-halo-1-alkyne with an alkyl magnesium halide again, and then reacting the resulting product with an alkyl orthoformate.

The acid catalyst to be used in the hydrolysis reaction for forming an aldehyde is not particularly limited. Specific examples thereof include an inorganic acid such as hydrochloric acid, sulfuric acid, nitric acid and perchloric acid; a carboxylic acid such as formic acid, acetic acid, oxalic acid, trifluoroacetic acid, difluoroacetic acid, trichloroacetic acid, dichloroacetic acid and monochloroacetic acid; and a sulfonic acid such as p-toluenesulfonic acid, methanesulfonic acid and benzenesulfonic acid. The acid may be used singly or in combination of two or more acids. Of these examples, a sulfonic acid such as p-toluenesulfonic acid, methanesulfonic acid and benzenesulfonic acid are particularly preferred from the standpoints of a reaction rate, an amount of impurity formed, and a yield. The acid catalyst is used in an amount of preferably from 0.01 to 0.1 mol per mol of the ω-halo-1,1-dialkoxy-2-alkyne (2). The acid catalyst is used in an amount of particularly preferably from 0.03 to 0.05 mol per mol of the ω-halo-1,1-dialkoxy-2-alkyne (2) from the standpoints of a reaction rate, an amount of impurity formed, and a yield.

In the hydrolysis reaction for forming an aldehyde, water is also used. Water is used in an amount of preferably from 30 to 300 g per mol of the ω-halo-1,1-dialkoxy-2-alkyne (2). Water is used in an amount of particularly preferably from 100 to 250 g per mol of the ω-halo-1,1-dialkoxy-2-alkyne (2) from the standpoints of a reaction rate and a yield per volume of a reactor.

In the hydrolysis reaction for forming an aldehyde, the organic solvent is not particularly limited insofar as it does not adversely affect the reaction. A water-soluble organic solvent is preferred from the standpoint of reactivity. Examples include methanol, ethanol, n-propyl alcohol, isopropyl alcohol, tetrahydrofuran, acetone, N,N-dimethylformamide and N,N-dimethylacetamide. Tetrahydrofuran is particularly preferred from the standpoint of reactivity. The organic solvent is used in an amount of preferably from 10 to 200 g per mol of the ω-halo-1,1-dialkoxy-2-alkyne (2). The organic solvent is used in an amount of particularly preferably from 30 to 100 g per mol of the ω-halo-1,1-dialkoxy-2-alkyne (2) from the standpoints of a reaction rate and a yield per volume of a reactor.

The temperature of the hydrolysis reaction for forming an aldehyde is preferably from 30 to 120° C. It is particularly preferably from 60 to 85° C. from the standpoints of a reaction rate, an amount of impurity formed, and a yield. An alcohol formed as a by-product in the hydrolysis reaction may be distilled off from a reactor under normal pressure or reduced pressure.

Next, the ω-halo-2-alkynal (1) is reacted with an alkylidene triphenylphosphorane (3) through a Wittig reaction to produce a conjugated Z-alken-yn-yl halide (4). For example, Z-13-hexadecen-11-yn-yl chloride can be produced by reacting 13-chloro-2-tridecynal with propylidene triphenylphosphorane.

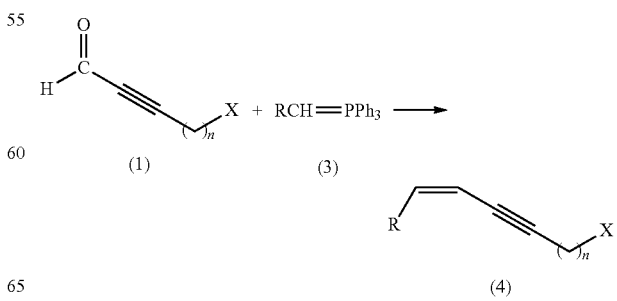

X and n have the same meanings as described above and preferred examples of each of them are also as described above. Ph represents a phenyl group.

R represents a linear, branched or cyclic $C_{1-12}$ hydrocarbon group. Specific examples thereof include a linear hydrocarbon group such as methyl, ethyl and propyl; a branched hydrocarbon group such as isopropyl, isobutyl, sec-butyl and tert-butyl; and a cyclic hydrocarbon group such as cyclopropyl, cyclobutyl, cyclopentyl and cyclohexyl. Preferred is a linear $C_{1-12}$ hydrocarbon group, with a linear $C_{1-6}$ hydrocarbon group being more preferred.

Specific examples of the alkylidene triphenylphosphorane (3) include ethylidene triphenylphosphorane, propylidene triphenylphosphorane, butylidene triphenylphosphorane, pentylidene triphenylphosphorane, propylidene triphenylphosphorane, isopropylmethylidene triphenylphosphorane, isobutylmethylidene triphenylphosphorane, sec-butylmethylidene triphenylphosphorane, tert-butylmethylidene triphenylphosphorane, cyclopropylmethylidene triphenylphosphorane, cyclobutylmethylidene triphenylphosphorane and cyclopentylmethylidene triphenylphosphorane.

Specific examples of the conjugated Z-alken-yn-yl halide (4) include a conjugated Z-alken-yn-yl chloride such as Z-7-decen-5-yn-yl chloride, Z-9-dodecen-7-yn-yl chloride, Z-9-undecen-7-yn-yl chloride, Z-10-dodecen-8-yn-yl chloride, Z-11-tridecen-9-yn-yl chloride, Z-12-tetradecen-10-yn-yl chloride, Z-13-pentadecen-11-yn-yl chloride, Z-9-dodecen-7-yn-yl chloride, Z-10-tridecen-8-yn-yl chloride, Z-11-tetradecen-9-yn-yl chloride, Z-12-pentadecen-10-yn-yl chloride, Z-13-hexadecen-11-yn-yl chloride, Z-9-tridecen-7-yn-yl chloride, Z-10-tetradecen-8-yn-yl chloride, Z-11-pentadecen-9-yn-yl chloride, Z-12-hexadecen-10-yn-yl chloride, Z-13-heptadecen-11-yn-yl chloride, Z-9-tetradecen-7-yn-yl chloride, Z-10-pentadecen-8-yn-yl chloride, Z-11-hexadecen-9-yn-yl chloride, Z-12-heptadecen-10-yn-yl chloride and Z-13-octadecen-11-yn-yl chloride; and a conjugated Z-alken-yn-yl bromide such as Z-7-decen-5-yn-yl bromide, Z-9-dodecen-7-yn-yl bromide, Z-9-undecen-7-yn-yl bromide, Z-10-dodecen-8-yn-yl bromide, Z-11-tridecen-9-yn-yl bromide, Z-12-tetradecen-10-yn-yl bromide, Z-13-pentadecen-11-yn-yl bromide, Z-9-dodecen-7-yn-yl bromide, Z-10-tridecen-8-yn-yl bromide, Z-11-tetradecen-9-yn-yl bromide, Z-12-pentadecen-10-yn-yl bromide, Z-13-hexadecen-11-yn-yl bromide, Z-9-tridecen-7-yn-yl bromide, Z-10-tetradecen-8-yn-yl bromide, Z-11-pentadecen-9-yn-yl bromide, Z-12-hexadecen-10-yn-yl bromide, Z-13-heptadecen-11-yn-yl bromide, Z-9-tetradecen-7-yn-yl bromide, Z-10-pentadecen-8-yn-yl bromide, Z-11-hexadecen-9-yn-yl bromide, Z-12-heptadecen-10-yn-yl bromide and Z-13-octadecen-11-yn-yl bromide.

The alkylidene triphenylphosphorane (3) can be produced in a known manner. For example, an alkyl halide is reacted with triphenylphosphine in a solvent to form an alkyl triphenylphosphonium halide, where the solvent includes an ether solvent such as tetrahydrofuran, diethyl ether and cyclopentyl methyl ether; an aromatic solvent such as benzene, toluene, and xylene; and an amide solvent such as N,N-dimethylformamide and N,N-dimethylacetamide. Then the alkyl triphenylphosphonium halide is reacted with a base to form the alkylidene triphenylphosphorane (3), where the base includes a metal alkoxide compound such as potassium t-butoxide and sodium methoxide; an organolithium compound such as methyllithium, n-butyllithium and phenyllithium; a metal hydride such as lithium hydride, sodium hydride and calcium hydride; and a metal amide compound such as sodium amide and lithium diisopropylamide.

A solvent for the reaction between the ω-halo-2-alkynal (1) and the alkylidene triphenylphosphorane (3) is not particularly limited insofar as it is not a protic solvent such as alcohol solvent adversely affecting the reaction. For example, the solvent preferably includes a hydrocarbon solvent such as toluene, xylene and hexane; an ether solvent such as tetrahydrofuran, diethyl ether and cyclopentyl methyl ether; and an amide solvent such as N,N-dimethylformamide and N,N-dimethylacetamide. The tetrahydrofuran is particularly preferred from the standpoint of reactivity. The solvent may be used singly or in combination of two or more thereof. The solvent is used in an amount of preferably from 300 to 1200 g per mol of the ω-halo-2-alkynal (1). The solvent is used in an amount of particularly preferably from 400 to 800 g per mol of the ω-halo-2-alkynal (1) from the standpoints of a reaction rate and a yield per volume of a reactor.

The reaction temperature is preferably from 0 to 50° C. It is particularly preferably from 0 to 10° C. from the standpoint of an amount of impurity formed and an amount of geometrical isomer formed.

Next, the conjugated Z-alken-yn-yl halide (4) can be reacted with a metal acetate or the like for acetoxylation to form an intended conjugated Z-alken-yn-yl acetate (5). For example, Z-13-hexadecen-11-yn-yl chloride can be acetoxylated to form an intended Z-13-hexadecen-11-yn-yl acetate.

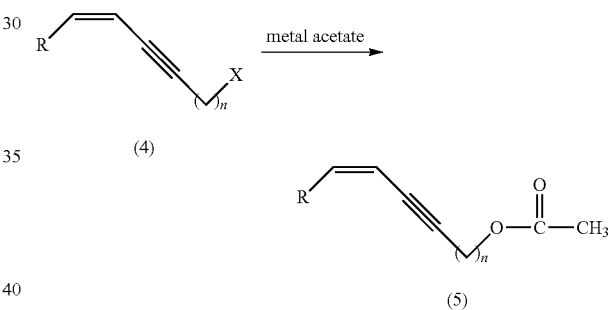

In the above formula, R, X and n have the same meanings as described above. Preferred examples of each of them are also as described above.

Specific examples of the conjugated Z-alken-yn-yl acetate (5) include Z-7-decen-5-yn-yl acetate, Z-9-dodecen-7-yn-yl acetate, Z-9-undecen-7-yn-yl acetate, Z-10-dodecen-8-yn-yl acetate, Z-11-tridecen-9-yn-yl acetate, Z-12-tetradecen-10-yn-yl acetate, Z-13-pentadecen-11-yn-yl acetate, Z-9-dodecen-7-yn-yl acetate, Z-10-tridecen-8-yn-yl acetate, Z-11-tetradecen-9-yn-yl acetate, Z-12-pentadecen-10-yn-yl acetate, Z-13-hexadecen-11-yn-yl acetate, Z-9-tridecen-7-yn-yl acetate, Z-10-tetradecen-8-yn-yl acetate, Z-11-pentadecen-9-yn-yl acetate, Z-12-hexadecen-10-yn-yl acetate, Z-13-heptadecen-11-yn-yl acetate, Z-9-tetradecen-7-yn-yl acetate, Z-10-pentadecen-8-yn-yl acetate, Z-11-hexadecen-9-yn-yl acetate, Z-12-heptadecen-10-yn-yl acetate and Z-13-octadecen-11-yn-yl acetate.

In this acetoxylation reaction, the metal acetate is preferably an alkali metal acetate. Examples of the alkali metal acetate include lithium acetate, sodium acetate and potassium acetate, and may be used singly or in combination of two or more thereof. The alkali metal acetate is used in an amount of preferably from 1.0 to 2.0 equivalents per mol of the conjugated Z-alken-yn-yl halide (4). The alkali metal acetate is used in an amount of particularly preferably from 1.1 to 1.3 equivalents per mol of the conjugated Z-alken-yn-yl halide (4) from the standpoints of reactivity and an amount of impurity formed.

A solvent for this acetoxylation reaction is not particularly limited. Examples of the solvent include acetonitrile, acetone, tetrahydrofuran, N,N-dimethylformamide, N,N-dimethylacetamide, dimethylsulfoxide, hexamethylphosphoric triamide and acetic acid. The N,N-Dimethylformamide and N,N-dimethylacetamide are preferred from the standpoint of reactivity. The solvent is used in an amount of from 50 to 300 g per mol of the conjugated Z-alken-yn-yl halide (4). The solvent is used in an amount of particularly preferably from 80 to 150 g per mol of the conjugated Z-alken-yn-yl halide (4) from the standpoints of a reaction rate and a yield per volume of a reactor.

The temperature of the acetoxylation reaction is preferably from 60 to 150° C. It is particularly preferably from 100 to 130° C. from the standpoint of a reaction rate and an amount of impurity formed.

EXAMPLES

The invention will hereinafter be described specifically by Examples. However, it should not be construed that the invention is limited to or by Examples below.

Synthesis Example 1

(Production of 7-chloro-1,1-diethoxy-2-heptyne)

In a reactor equipped with a stirrer, a cooling condenser, a dropping funnel and a thermometer was placed a solution of methyl magnesium chloride (89.7 g:1.2 mol) in tetrahydrofuran (370.0 g), and stirred at a solution temperature of from 45 to 50° C. The 6-chloro-1-hexyne (116.6 g:1.0 mol) was dropwise added thereto at a reaction mixture temperature of from 50 to 60° C. over one hour, and then stirred at from 60 to 65° C. for 5 hours. A solution of triethyl orthoformate (177.8 g:1.2 mol) in toluene (120.0 g) was dropwise added thereto at a reaction mixture temperature of from 80 to 85° C. over 30 minutes, and then stirred at from 90 to 95° C. for 6 hours. After completion of the reaction was confirmed by gas chromatography, acetic acid (57.0 g), ammonium chloride (35.0 g) and water (400.0 g) were added to the reaction mixture.

The organic phase separated from the aqueous phase was washed with an aqueous 1.0% sodium hydroxide solution (170.0 g). The organic phase was subjected to removal of the solvent under reduced pressure, and then the residue was distilled under reduced pressure to obtain 7-chloro-1,1-diethoxy-2-heptyne [bp: 100-104° C./0.13 KPa, 133.4 g, 0.61 mol]. [Yield: 61.0%]

The structure of the 7-chloro-1,1-diethoxy-2-heptyne thus obtained was confirmed by a $^1$H nuclear magnetic resonance spectrum, a $^{13}$C nuclear magnetic resonance spectrum and a mass spectrum.

[Nuclear Magnetic Resonance Spectrum]

$^1$H NMR (500 MHz, CDCl$_3$): δ1.22 (3H, t), 1.68 (2H, tt), 1.88 (2H, tt), 2.29 (2H, t), 3.56 (4H, dq), 3.72 (2H, tt), 5.23 (1H, s)

$^{13}$C NMR (126 MHz, CDCl$_3$): δ15.05, 15.05, 17.90, 25.42, 31.49, 44.38, 60.60, 60.60, 76.37, 85.35, 91.37

[Mass spectrum] EI (70 eV) m/z: 217 (M$^+$-1), 173 (M$^+$-45), 145, 117, 81, 68, 55, 41, 29

Synthesis Example 2

(Production of 9-chloro-1,1-diethoxy-2-nonyne)

In a reactor equipped with a stirrer, a cooling condenser, a dropping funnel and a thermometer was placed a solution of methyl magnesium chloride (89.7 g:1.2 mol) in tetrahydrofuran (370.0 g), and stirred at a solution temperature of from 45 to 50° C.

The 8-chloro-1-octyne (144.6 g:1.0 mol) was dropwise added thereto at a reaction mixture temperature of from 50 to 60° C. over one hour, and then stirred at from 60 to 65° C. for 5 hours. A solution of triethyl orthoformate (177.8 g:1.2 mol) in toluene (120.0 g) was then dropwise added thereto at a reaction mixture of from 80 to 85° C. over 30 minutes, and stirred at from 90 to 95° C. for 6 hours. After completion of the reaction was confirmed by gas chromatography, acetic acid (57.0 g), ammonium chloride (35.0 g) and water (400.0 g) were added to the reaction mixture. The organic phase separated from the aqueous phase was washed with an aqueous 1.0% sodium hydroxide solution (170.0 g). The organic phase was subjected to removal of the solvent under reduced pressure, and then the residue was distilled under reduced pressure to obtain 9-chloro-1,1-diethoxy-2-nonyne [bp: 138-142° C./0.13 KPa, 185.8 g, 0.75 mol]. [Yield: 75.3%]

The structure of the 9-chloro-1,1-diethoxy-2-nonyne thus obtained was confirmed by a $^1$H nuclear magnetic resonance spectrum, a $^{13}$C nuclear magnetic resonance spectrum and a mass spectrum.

[Nuclear Magnetic Resonance Spectrum]

$^1$H NMR (500 MHz, CDCl$_3$): δ1.22 (3H, t), 1.40-1.43 (4H, m), 1.53 (2H, tt), 1.76 (2H, tt), 2.24 (2H, t), 3.54 (4H, dq), 3.72 (2H, tt), 5.24 (1H, s)

$^{13}$C NMR (126 MHz, CDCl$_3$): δ15.05, 15.05, 18.24, 18.64, 26.28, 28.02, 32.38, 44.90, 60.54, 60.54, 75.87, 86.08, 91.40

[Mass spectrum] EI (70 eV) m/z: 245 (M$^+$-1), 201 (M$^+$-45), 173, 109, 93, 81, 67, 55, 41, 29

Synthesis Example 3

(Production of 13-chloro-1,1-diethoxy-2-tridecyne)

In a reactor equipped with a stirrer, a cooling condenser, a dropping funnel and a thermometer was placed a solution of methyl magnesium chloride (89.7 g:1.2 mol) in tetrahydrofuran (370.0 g), and stirred at a solution temperature of from 45 to 50° C. The 12-chloro-1-dodecyne (200.8 g:1.0 mol) was dropwise added thereto at a reaction mixture temperature of from 50 to 60° C. over 1 hour, and then stirred at from 60 to 65° C. for 5 hours. Then, a solution of triethyl orthoformate (177.8 g:1.2 mol) in toluene (120.0 g) was dropwise added at a reaction mixture of from 80 to 85° C. over 30 minutes, and then stirred at from 90 to 95° C. for 6 hours. After completion of the reaction was confirmed by gas chromatography, acetic acid (57.0 g), ammonium chloride (35.0 g) and water (400.0 g) were added to the reaction mixture. The organic phase separated from the aqueous phase was washed with an aqueous 1.0% sodium hydroxide solution (170.0 g). The organic phase was subjected to removal of the solvent under reduced pressure, and then the residue was distilled under reduced pressure to obtain 13-chloro-1,1-diethoxy-2-tridecyne [bp: 156-163° C./0.13 KPa, 249.2 g, 0.82 mol]. [Yield: 82.3%]

The structure of the 13-chloro-1,1-diethoxy-2-tridecyne thus obtained was confirmed by a $^1$H nuclear magnetic resonance spectrum, a $^{13}$C nuclear magnetic resonance spectrum and a mass spectrum.

[Nuclear Magnetic Resonance Spectrum]
$^1$H NMR (500 MHz, CDCl$_3$): δ1.22 (3H, t), 1.24-1.29 (8H, m), 1.32-1.44 (4H, m), 1.51 (2H, tt), 1.75 (2H, tt), 2.20 (2H, t), 3.53 (4H, dq), 3.72 (2H, tt), 5.24 (1H, s)
$^{13}$C NMR (126 MHz, CDCl$_3$): δ15.05, 15.05, 18.55, 26.81, 28.23, 28.78, 28.80, 28.97, 29.30, 29.33, 32.58, 45.09, 60.51, 60.51, 75.66, 86.44, 91.43
[Mass spectrum] EI (70 eV) m/z: 301 (M$^+$−1), 257 (M$^+$−45), 155, 81, 55, 29

Example 1

(Production of 7-chloro-2-heptynal)
In a reactor equipped with a stirrer, a cooling condenser, a dropping funnel and a thermometer were placed 7-chloro-1,1-diethoxy-2-heptyne (218.7 g:1.0 mol), para-toluenesulfonic acid (8.0 g:0.05 mol), water (170.0 g) and tetrahydrofuran (42.0 g), and stirred at a reaction mixture temperature of from 60 to 65° C. During stirring, the pressure in the reactor was reduced gradually to 26.7 KPa to distill off refluxing ethanol. After stirring for 5 hours, completion of the reaction was confirmed by gas chromatography. The organic phase separated from the aqueous phase of the reaction mixture was washed with a solution of sodium chloride (5.0 g) in water (150.0 g). The organic phase was subjected to removal of the solvent under reduced pressure, and then the residue was distilled under reduced pressure to obtain 7-chloro-2-heptynal [bp: 66-72° C./0.13 KPa, 137.8 g, 0.95 mol]. [Yield: 95.3%]
The structure of the 7-chloro-2-heptynal thus obtained was confirmed by a $^1$H nuclear magnetic resonance spectrum, a $^{13}$C-nuclear magnetic resonance spectrum and a mass spectrum.
[Nuclear Magnetic Resonance Spectrum]
$^1$H NMR (500 MHz, CDCl$_3$): δ1.75 (2H, tt), 1.89 (2H, tt), 2.46 (2H, t), 3.55 (2H, t), 9.15 (1H, s)
$^{13}$C NMR (126 MHz, CDCl$_3$): δ18.23, 24.66, 31.24, 44.07, 81.86, 97.79, 177.01 [Mass spectrum] EI (70 eV) m/z: 143 (M$^+$−1), 115, 107, 81, 68, 53, 41

Example 2

(Production of 9-chloro-2-nonynal)
In a reactor equipped with a stirrer, a cooling condenser, a dropping funnel and a thermometer were placed 9-chloro-1,1-diethoxy-2-nonyne (246.8 g:1.0 mol), para-toluenesulfonic acid (8.0 g:0.05 mol), water (170.0 g) and tetrahydrofuran (42.0 g), and stirred at a reaction mixture temperature of from 60 to 65° C. During stirring, the pressure in the reactor was reduced gradually to 26.7 KPa to distill off refluxing ethanol. After stirring for 5 hours, completion of the reaction was confirmed by gas chromatography. The organic phase separated from the aqueous phase of the reaction mixture was washed with a solution of sodium chloride (5.0 g) in water (150.0 g). The organic phase was subjected to removal of the solvent under reduced pressure, and then the residue was distilled under reduced pressure to obtain 9-chloro-2-nonynal [bp: 82-88° C./0.13 KPa, 167.2 g, 0.97 mol]. [Yield: 96.9%]
The structure of the 9-chloro-2-nonynal thus obtained was confirmed by a $^1$H-nuclear magnetic resonance spectrum, a $^{13}$C-nuclear magnetic resonance spectrum and a mass spectrum.
[Nuclear Magnetic Resonance Spectrum]
$^1$H NMR (500 MHz, CDCl$_3$): δ1.40-1.49 (4H, m), 1.60 (2H, tt), 1.77 (2H, tt), 2.41 (2H, t), 3.52 (2H, t), 9.16 (1H, s)
$^{13}$C NMR (126 MHz, CDCl$_3$): δ18.95, 26.19, 27.26, 27.96, 32.24, 44.86, 81.70, 98.85, 177.17
[Mass spectrum] EI (70 eV) m/z: 171 (M$^+$−1), 143, 123, 109, 95, 81, 67, 55, 41

Example 3

(Production of 13-chloro-2-tridecynal)
In a reactor equipped with a stirrer, a cooling condenser, a dropping funnel and a thermometer were placed 13-chloro-1,1-diethoxy-2-tridecyne (302.9 g:1.0 mol), para-toluenesulfonic acid (8.0 g:0.05 mol), water (170.0 g) and tetrahydrofuran (42.0 g), and then stirred at a reaction mixture temperature of from 60 to 65° C. During stirring, the pressure in the reactor was reduced gradually to 26.7 KPa to distill off refluxing ethanol. After stirring for 5 hours, completion of the reaction was confirmed by gas chromatography. The organic phase separated from the aqueous phase of the reaction mixture was washed with a solution of sodium chloride (5.0 g) in water (150.0 g). The organic phase was subjected to removal of the solvent under reduced pressure, and then the residue was distilled under reduced pressure to obtain 13-chloro-2-tridecynal [bp: 116-122° C./0.13 KPa, 198.6 g, 0.87 mol]. [Yield: 86.8%]
The structure of the 13-chloro-2-tridecynal thus obtained was confirmed by a $^1$H nuclear magnetic resonance spectrum, a $^{13}$C-nuclear magnetic resonance spectrum and a mass spectrum.
[Nuclear Magnetic Resonance Spectrum]
$^1$H NMR (500 MHz, CDCl$_3$): δ1.26-1.32 (8H, m), 1.35-1.45 (4H, m), 1.58 (2H, tt), 1.75 (2H, tt), 2.39 (2H, t), 3.52 (2H, t), 9.17 (1H, s)
$^{13}$C NMR (126 MHz, CDCl$_3$): δ19.07, 26.79, 27.47, 28.74, 28.78, 28.99, 29.23, 29.30, 32.57, 45.11, 81.66, 99.29, 117.20
[Mass spectrum] EI (70 eV) m/z: 227 (M$^+$), 199, 185, 151, 137, 123, 109, 95, 81, 67, 55, 41, 29

Example 4

(Production of Z-7-decen-5-yn-yl chloride)
In a reactor equipped with a stirrer, a cooling condenser, a dropping funnel and a thermometer were placed triphenylphosphine (314.8 g:1.2 mol), n-propyl bromide (147.6 g:1.2 mol) and N,N-dimethylacetamide (200.0 g), and stirred at a reaction mixture temperature of from 110 to 120° C. for 3 hours. The reaction mixture was then cooled to 10° C. and subjected to addition of tetrahydrofuran (600.0 g), followed by addition of potassium t-butoxide (134.8 g:1.2 mol) at a reaction mixture temperature of from 10 to 15° C. over 20 minutes. The resulting mixture was stirred for one hour. After stirring, the reaction mixture was cooled to 0° C., and 7-chloro-2-heptynal (144.6 g: 1.0 mol) was dropwise added thereto at a reaction mixture temperature of from 0 to 10° C. over one hour. After the dropwise addition, the reaction mixture was stirred for one hour. The reaction was then terminated with water (300 g). The organic phase separated from the aqueous phase was subjected to removal of the solvent under reduced pressure. Triphenylphosphine oxide, which was a by-product precipitated by the removal of the solvent, was filtered out. The filtrate was then distilled under reduced pressure to obtain Z-7-decen-5-yn-yl chloride [bp: from 67 to 72° C./0.40 KPa, 128.1 g, 0.75 mol]. [Yield: 75.1%]
The structure of the Z-7-decen-5-yn-yl chloride thus obtained was confirmed by a $^1$H nuclear magnetic resonance spectrum, a $^{13}$C nuclear magnetic resonance spectrum and a mass spectrum.

[Nuclear Magnetic Resonance Spectrum]

$^1$H NMR (500 MHz, CDCl$_3$): δ1.01 (3H, t), 1.70 (2H, tt), 1.91 (2H, tt), 2.28 (2H, dq), 2.39 (2H, dt), 3.57 (2H, t), 5.39 (1H, dt), 5.82 (1H, dt)

$^{13}$C NMR (126 MHz, CDCl$_3$): δ13.41, 18.80, 23.45, 25.96, 31.56, 44.53, 77.84, 93.27, 108.48, 144.42

[Mass spectrum] EI (70 eV) m/z: 170 (M$^+$), 135, 119, 105, 91, 79, 65, 51, 39, 27

Example 5

(Production of Z-9-dodecen-7-yn-yl chloride)

In a reactor equipped with a stirrer, a cooling condenser, a dropping funnel and a thermometer were placed triphenylphosphine (314.8 g:1.2 mol), n-propyl bromide (147.6 g:1.2 mol) and N,N-dimethylacetamide (200.0 g), and stirred at a reaction mixture temperature of from 110 to 120° C. for 3 hours. The reaction mixture was then cooled to 10° C. and subjected to addition of tetrahydrofuran (600.0 g), followed by addition of potassium t-butoxide (134.8 g:1.2 mol) at a reaction mixture temperature of from 10 to 15° C. over 20 minutes. The resulting mixture was stirred for one hour. After stirring, the reaction mixture was cooled to 0° C., and 9-chloro-2-nonynal (172.6 g: 1.0 mol) was dropwise added thereto at a reaction mixture temperature of from 0 to 10° C. over one hour. After the dropwise addition, the reaction mixture was stirred for one hour. The reaction was then terminated with water (300 g). The organic phase separated from the aqueous phase was subjected to removal of the solvent under reduced pressure. Triphenylphosphine oxide, which was a by-product precipitated by the removal of the solvent, was filtered out. The filtrate was then distilled under reduced pressure to obtain Z-9-dodecen-7-yn-yl chloride [bp: from 77 to 83° C./0.13 KPa, 172.1 g, 0.87 mol]. [Yield: 86.6%]

The structure of the Z-9-dodecen-7-yn-yl chloride thus obtained was confirmed by a $^1$H nuclear magnetic resonance spectrum, a $^{13}$C nuclear magnetic resonance spectrum and a mass spectrum.

[Nuclear Magnetic Resonance Spectrum]

$^1$H NMR (500 MHz, CDCl$_3$): δ1.01 (3H, t), 1.41-1.49 (4H, m), 1.51-1.60 (2H, m), 1.75-1.82 (2H, m), 2.29 (2H, dq), 2.34 (2H, dt), 5.40 (1H, dt), 5.80 (1H, dt)

$^{13}$C NMR (126 MHz, CDCl$_3$): δ13.43, 19.40, 23.42, 26.38, 28.04, 28.59, 32.48, 45.00, 77.39, 94.08, 108.62, 144.17

[Mass spectrum] EI (70 eV) m/z: 198 (M$^+$), 169, 135, 121, 107, 93, 79, 67, 55, 41, 27

Example 6

(Production of Z-13-hexadecen-11-yn-yl chloride)

In a reactor equipped with a stirrer, a cooling condenser, a dropping funnel and a thermometer were placed triphenylphosphine (314.8 g:1.2 mol), n-propyl bromide (147.6 g:1.2 mol) and N,N-dimethylacetamide (200.0 g), and stirred at a reaction mixture temperature of from 110 to 120° C. for 3 hours. The reaction mixture was then cooled to 10° C., and subjected to addition of tetrahydrofuran (600.0 g), followed by addition of potassium t-butoxide (134.8 g:1.2 mol) at a reaction mixture temperature of from 10 to 15° C. over 20 minutes. The resulting mixture was stirred for one hour. After stirring, the reaction mixture was cooled to 0° C., and 13-chloro-2-tridecynal (228.8 g:1.0 mol) was dropwise added thereto at a reaction mixture temperature of from 0 to 10° C. over one hour. After the dropwise addition, the reaction mixture was stirred for one hour. The reaction was then terminated with water (300 g). The organic phase separated from the aqueous phase was subjected to removal of the solvent under reduced pressure. Triphenylphosphine oxide, which was a by-product precipitated by the removal of the solvent, was filtered out. The filtrate was then distilled under reduced pressure to obtain Z-13-hexadecen-11-yn-yl chloride [bp: from 118 to 122° C./0.13 KPa, 210.5 g, 0.83 mol]. [Yield: 82.6%]

The structure of the Z-13-hexadecen-11-yn-yl chloride thus obtained was confirmed by a $^1$H-nuclear magnetic resonance spectrum, a $^{13}$C-nuclear magnetic resonance spectrum and a mass spectrum.

[Nuclear Magnetic Resonance Spectrum]

$^1$H NMR (500 MHz, CDCl$_3$): δ1.00 (3H, t), 1.25-1.34 (10H, m), 1.36-1.46 (4H, m), 1.53 (2H, tt), 1.76 (2H, tt), 2.29 (2H, dq), 2.32 (2H, t), 3.52 (2H, t), 5.40 (1H, td), 5.80 (1H, dt)

$^{13}$C NMR (126 MHz, CDCl$_3$): δ13.44, 19.48, 23.39, 26.85, 28.80, 28.85, 28.85, 29.06, 29.38, 29.38, 32.62, 45.14, 77.26, 94.45, 108.69, 144.04

[Mass spectrum] EI (70 eV) m/z: 254 (M$^+$), 225, 211, 163, 149, 135, 121, 107, 93, 79, 55, 41, 27

Example 7

(Production of Z-7-decen-5-yn-yl acetate)

In a reactor equipped with a stirrer, a cooling condenser, a dropping funnel and a thermometer were placed Z-7-decen-5-yn-yl chloride (170.7 g:1.0 mol), sodium acetate (98.4 g:1.2 mol), sodium iodide (8.9 g:0.06 mol) and N,N-dimethylacetamide (113.2 g), and stirred at from 120 to 125° C. for 6 hours. After the completion of the reaction was confirmed by gas chromatography, water (350.0 g) was added to the reaction mixture. The organic phase separated from the aqueous phase was washed with an aqueous 1.0% by weight sodium bicarbonate solution (250.0 g). The organic phase was subjected to removal of solvent under reduced pressure, followed by dehydration. The residue was then distilled under reduced pressure to obtain Z-7-decen-5-yn-yl acetate [bp: from 75 to 79° C./0.13 KPa, 181.4 g, 0.93 mol]. [Yield: 93.4%]

The structure of the Z-7-decen-5-yn-yl acetate thus obtained was confirmed by a $^1$H nuclear magnetic resonance spectrum, a $^{13}$C nuclear magnetic resonance spectrum and a mass spectrum.

[Nuclear Magnetic Resonance Spectrum]

$^1$H NMR (500 MHz, CDCl$_3$): δ0.99 (3H, t), 1.60 (2H, tt), 0.75 (2H, tt), 2.03 (1H, s), 2.27 (2H, dq), 2.37 (2H, t), 4.08 (2H, t), 5.38 (1H, dt), 5.81 (1H, td)

$^{13}$C NMR (126 MHz, CDCl$_3$): δ13.38, 19.14, 20.91, 23.40, 25.28, 27.74, 63.98, 77.69, 93.46, 108.50, 144.30, 171.10

[Mass spectrum] EI (70 eV) m/z: 194 (M$^+$), 165, 151, 134, 119, 108, 91, 79, 65, 55, 43, 27

Example 8

(Production of Z-9-dodecen-7-yn-yl acetate)

In a reactor equipped with a stirrer, a cooling condenser, a dropping funnel and a thermometer were placed Z-9-decen-7-yn-yl chloride (198.7 g:1.0 mol), sodium acetate (98.4 g:1.2 mol), sodium iodide (8.9 g:0.06 mol) and N,N-dimethylacetamide (113.2 g), and stirred at from 120 to 125° C. for 6 hours. After the completion of the reaction was confirmed by gas chromatography, water (350.0 g) was added to the reaction mixture. The organic phase separated from the aqueous phase was washed with an aqueous 1.0% by weight sodium bicarbonate solution (250.0 g). The organic phase was subjected to removal of the solvent under reduced pressure, followed by dehydration. The residue was then distilled under reduced pressure to obtain Z-9-dodecen-7-yn-yl acetate [bp: from 94 to 102° C./0.13 KPa, 202.3 g, 0.91 mol]. [Yield: 91.1%]

The structure of the Z-9-dodecen-7-yn-yl acetate thus obtained was confirmed by a $^1$H nuclear magnetic resonance spectrum, a $^{13}$C nuclear magnetic resonance spectrum and a mass spectrum.

[Nuclear Magnetic Resonance Spectrum]

$^1$H NMR (500 MHz, CDCl$_3$): δ0.99 (3H, t), 1.32-1.47 (4H, m), 1.54 (2H, tt), 1.62 (2H, tt), 2.03 (3H, s), 2.27 (2H, dq), 2.32 (2H, t), 4.04 (2H, t), 5.38 (1H, dt), 5.79 (1H, dt)

$^{13}$C NMR (126 MHz, CDCl$_3$): δ13.39, 19.38, 20.93, 23.38, 25.43, 28.40, 28.47, 28.64, 64.46, 77.31, 94.11, 108.61, 144.08, 171.14

[Mass spectrum] EI (70 eV) m/z: 222 (M$^+$), 179, 162, 147, 133, 119, 105, 91, 79, 67, 55, 43, 29

Example 9

(Production of Z-13-hexadecen-11-yn-yl acetate)

In a reactor equipped with a stirrer, a cooling condenser, a dropping funnel and a thermometer were placed Z-13-hexadecen-11-yn-yl chloride (254.8 g:1.0 mol), sodium acetate (98.4 g:1.2 mol), sodium iodide (8.9 g:0.06 mol) and N,N-dimethylacetamide (113.2 g), and stirred at from 120 to 125° C. for 6 hours. After the completion of the reaction was confirmed by gas chromatography, water (350.0 g) was added to the reaction mixture. The organic phase separated from the aqueous phase was washed with an aqueous 1.0% by weight sodium bicarbonate solution (250.0 g). The organic phase was subjected to removal of the solvent under reduced pressure, followed by dehydration. The residue was then distilled under reduced pressure to obtain Z-13-hexadecen-11-yn-yl acetate [bp: from 126 to 130° C./0.13 KPa, 261.2 g, 0.94 mol]. [Yield: 93.8%]

The structure of the Z-13-hexadecen-11-yn-yl acetate thus obtained was confirmed by a $^1$H nuclear magnetic resonance spectrum, a $^{13}$C nuclear magnetic resonance spectrum and a mass spectrum.

[Nuclear Magnetic Resonance Spectrum]

$^1$H NMR (500 MHz, CDCl$_3$): δ0.99 (3H, t), 1.25-1.43 (12H, m), 1.52 (2H, tt), 1.60 (2H, tt), 2.03 (3H, s), 2.28 (2H, dq), 2.30 (2H, t), 4.04 (2H, t), 5.39 (1H, dt), 5.79 (1H, dt)

$^{13}$C NMR (126 MHz, CDCl$_3$): δ13.42, 19.47, 20.97, 23.38, 25.87, 28.55, 28.79, 28.82, 29.05, 29.19, 29.40, 29.40, 64.60, 77.18, 94.44, 108.69, 144.00, 171.18

[Mass spectrum] EI (70 eV) m/z: 278 (M$^+$), 189, 175, 161, 147, 133, 119, 105, 94, 79, 65, 43, 29

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. A method for producing an ω-halo-2-alkynal, comprising a step of hydrolyzing an ω-halo-1,1-dialkoxy-2-alkyne represented by formula (2):

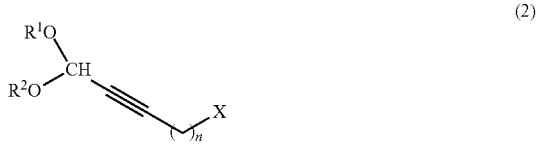

(2)

wherein R$^1$ and R$^2$ are the same or different and each represents a linear, branched or cyclic C$_{1-10}$ hydrocarbon group, X represents a halogen atom, and it stands for an integer of from 2 to 15, into a ω-halo-2-alkynal represented by formula (1):

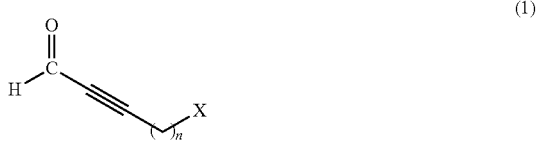

(1)

in water and an organic solvent in the presence of a sulfonic acid selected from the group consisting of p-toluenesulfonic acid, methanesulfonic acid and benzensulfonic acid.

* * * * *